United States Patent
Sharma et al.

(10) Patent No.: US 11,618,907 B2
(45) Date of Patent: Apr. 4, 2023

(54) PROCESS FOR XYLITOL PRODUCTION FROM XYLOSE

(71) Applicants: Indian Oil Corporation Limited, Mumbai (IN); Department Of Biotechnology, New Delhi (IN)

(72) Inventors: Ajay Kumar Sharma, Faridabad (IN); Manas Ranjan Swain, Faridabad (IN); Ajit Singh, Faridabad (IN); Anshu Shankar Mathur, Faridabad (IN); Ravi Prakash Gupta, Faridabad (IN); Suresh Kumar Puri, Faridabad (IN); Sankara Sri Venkata Ramakumar, Faridabad (IN)

(73) Assignees: Indian Oil Corporation Limited, Mumbai (IN); Department Of Biotechnology, New Delhi (IN)

( * ) Notice: Subject to any disclaimer, the term of this patent is extended or adjusted under 35 U.S.C. 154(b) by 0 days.

(21) Appl. No.: 17/394,811

(22) Filed: Aug. 5, 2021

(65) Prior Publication Data

US 2022/0042050 A1    Feb. 10, 2022

(30) Foreign Application Priority Data

Aug. 7, 2020 (IN) .............................. 202021033994

(51) Int. Cl.
*C12P 7/18* (2006.01)
*C12P 7/14* (2006.01)
*C12R 1/865* (2006.01)

(52) U.S. Cl.
CPC ............... *C12P 7/18* (2013.01); *C12P 7/14* (2013.01); *C12R 2001/865* (2021.05)

(58) Field of Classification Search
CPC .................................... C12P 7/14; C12P 7/18
See application file for complete search history.

(56) References Cited

U.S. PATENT DOCUMENTS

| 7,482,144 | B2 | 1/2009 | Ojamo et al. |
| 8,921,082 | B2 | 12/2014 | Huang et al. |
| 9,228,178 | B2 | 1/2016 | Abbas et al. |
| 2007/0141690 | A1 | 6/2007 | Karhumaa et al. |
| 2015/0218598 | A1 | 8/2015 | Petkar et al. |

OTHER PUBLICATIONS

Converti, Attilio et al., "Influence of Temperature and pH on Xylitol Production from Xylose by Debaryomyces hansenii", Biotechnology and Bioengineering, Oct. 5, 2001, pp. 39-45, vol. 75, No. 1.

Cortivo, Paulo Roberto Dall et al., "Fermentation of oat and soybean hull hydrolysates into ethanol and xylitol by recombinant industrial strains of Saccharomyces cerevisiae under diverse oxygen environments", Industrial Crops & Products, 2018, pp. 10-18, vol. 113.

Dasgupta, Diptarka et al., "Lignocellulosic sugar management for xylitol and ethanol fermentation with muitiple cell recycling by Kiuyveromyces marxianus IIPE453", Microbiological Research, htlp://dx.doi.org/10.1016/j.micres.2017.04.002.

Dymtruk, Olena V et al., "Engineering of xylose reductase and overexpression of xylitol dehydrogenase and xylulokinase improves xylose alcoholic fermentation in the thermotolerant yeast Hansenula polymorpha", Microbial Cell Factories, Jul. 23, 2008, vol. 7:21.

Hallborn, Johan et al., "Xylitol Production by recombinant Saccharomyces cerevisiae", Nature Biotechnology, Nov. 1991, pp. 1090-1095, vol. 9.

Hickert, Lilian Raquel et al., "Simultaneous saccharification and co-fermentation of un-detoxified rice hull hydrolysate by Saccharomyces cerevisiae ICV D254 and Spathaspora arborariae NRRL Y-48658 for the production of ethanol and xylitol", Bioresource Technology, 2013, pp. 112-116, vol. 143.

Lee, Woo-Jong et al., "Characterization of two-substrate fermentation processes for xylitol production using recombinant Saccharomyces cere6isiae containing xylose reductase gene", Process Biochemistry, 2000, pp. 1199-1203, vol. 35.

Meyrial, V. et al., "Xylitol Production From D-Xylose By Candida G Llermondii: Fermentation Behaviour", Biotechnology Letters, Mar. 12, 1991, pp. 281-286, vol. 13, No. 4.

Mishra, A. et al, "Lignocellulosic bioethanol production employing newly isolated inhibitor and thermotolerant Saccharomyces cerevisiae DBTIOC S24 strain in SSF and Shf", RSC Advances, 2016, DOI: 10.1039/C6RA00007J.

Sampaio, Fabio C. et al., "Optimal activity and thermostability of xylose reductase from Debaryomyces hansenii UFV-170", J Ind Microbiol Biotechnol, 2009, pp. 293-300, vol. 36.

Swain, Manas R. et al., "Improved conversion of rice straw to ethanol and xylitol bycombination of moderate temperature ammonia pretreatment andsequential fermentation using Candida tropicalis", Industrial Crops and Products, 2015, pp. 1039-1046, vol. 77.

Zahed, Omid et al., "Continuous co-production of ethanol and xylitol from rice straw hydrolysate in a membrane bioreactor", Folia Microbiol, Sep. 9, 2015, DOI 10.1007/s12223-015-0420-0.

*Primary Examiner* — Tekchand Saidha
(74) *Attorney, Agent, or Firm* — Workman Nydegger

(57) ABSTRACT

The present invention discloses a process of xylitol production from pure xylose, xylose containing liquid extract from the acid pretreated biomass (LEPB) and co-production of ethanol and xylitol from dilute acid pretreated lignocellulosic biomass by natural *S. cerevisiae* DBT-IOC S24 (MTCC25086). The present invention also discloses a process of xylitol production wherein a thermo and inhibitor tolerant *S. cerevisiae* DBT-IOC S24 (MTCC25086) natural strain has been induced to produce xylitol from xylose at defined process parameters using xylose containing diluted acid pretreated biomass as well as from xylose containing synthetic media in presence of glucose, lignocelluloses biomass derived xylitol inducer maintaining aeration at 1VVM and pH at 5.0 in the medium.

11 Claims, 3 Drawing Sheets

PROCESS FOR XYLITOL PRODUCTION FROM XYLOSE

TECHNICAL FIELD

The present invention discloses a process of xylitol production from pure xylose, xylose containing liquid extract from the acid pretreated biomass (LEPB) and co-production of ethanol and xylitol from dilute acid pretreated lignocellulosic biomass by wild yeast strain *S. cerevisiae* DBT-IOC S24 (MTCC25086). Present invention also discloses a process of xylitol production wherein a thermo—and inhibitor tolerant *S. cerevisiae* DBT-IOC S24 (MTCC25086) natural strain has been induced to produce xylitol from xylose at defined process parameters. Said xylitol production from pure xylose, xylose rich acid pretreated biomass (LEPB) and co-production of ethanol and xylitol from dilute acid pretreated lignocellulosic biomass happens when the wild yeast strain *S. cerevisiae* DBT-IOC S24 (MTCC25086) is induced by glucose and lignocelluloses biomass derived xylitol inducer.

BACKGROUND ART

Xylose is second most abundant sugar in the world after glucose. The fermentation of xylose to ethanol is challenging due to lack of efficient natural strain. Several attempts have been made to develop genetically engineered strain of *S. cerevisiae* for conversion of xylose to ethanol.

U.S. Pat. No. 9,228,178 discloses recombinant genetic constructs and strains of *H. polymorpha* having significantly increased ethanol productivity with a simultaneous decreased production of xylitol during high-temperature xylose fermentation.

US 20070141690 discloses a new xylose utilizing genetically engineered *Saccharomyces cerevisiae* strain being able to utilize xylose for ethanol production which strain is up-regulated with regard to the genes for xylose reductase (XR) and xylitol dehydrogenase (XDH) as well as xylulokinase (XK) and over-expressing the non-oxidative pentose phosphate pathway (PPP) and comprising a deletion of the gene GRE3 deletion, as well as the strain adapted to xylose feeding.

U.S. Pat. No. 7,482,144 discloses that genetic modification of microorganisms is a preferred method to enhance their potential as xylitol producers, and to a process for the production of xylitol using said microorganisms.

U.S. Pat. No. 8,921,082 discloses that by using the yeast *Candida* sp., xylose can be effectively converted into xylitol. This document also provides the *Candida* strain having high furfural tolerance, and is capable to produce xylitol from various types of non-detoxified lignocellulosic hydrolysates. However, natural *Candida* sp. has been reported xylitol producing strain in its natural form. *Candida* strain has capability to produce xylitol due to presence of Xylose reductase gene.

In the research paper by Mishra et al, (2016), lignocellulosic bioethanol production employing newly isolated inhibitor and thermotolerant *Saccharomyces cerevisiae* DBTIOC S24 strain in SSF and SHF, (RSC Advances, Issue 29, 2016), authors investigates lignocellulosic ethanol production using inhibitor and thermotolerant *S. cerevisiae* DBTIOC S24 from non-detoxified and unsterilized rice straw hydrolysate.

Barbosa et. al., (1988) screened yeasts for production of xylitol from D-xylose and some factors which affect xylitol yield in *Candida guilliermondii*, this study also reported the ability of yeasts from five genera to convert D-xylose to xylitol and found that the best xylitol producers were localized largely in the species *Candida guilliermondii* and *C. tropicalis*. Barbosa et. al., (1988) also reported xylose theoretically yield as 0.905 g/g xylose.

Several attempts have been made to develop xylitol producing *S. cerevisiae* strain by genetic modification. These genetically modified strains have limitations to use at industrial level and needs regulatory approvals. In present invention, a natural thermo and inducer/inhibitor tolerant in-house strain *S. cerevisiae* DBT-IOC S24 is induced for xylitol production using inducer compounds generated during acid-pretreatment; these inducers transformed into less toxic compounds by this strain and xylose also converted into xylitol. The microbial strain *S. cerevisiae* DBT-IOC S24 (MTCC25086) was deposited at Microbial Type Culture Collection & Gene Bank (MTCC), Institute of Microbial Technology, Sector 39-A, Chandigarh-160036 on Mar. 17, 2016).

SUMMARY

The present invention discloses a process of xylitol production from pure xylose, xylose rich acid pretreated biomass (LEPB) and co-production of ethanol and xylitol from dilute acid pretreated lignocellulosic biomass by natural *S. cerevisiae* DBT-IOC S24 (MTCC25086). In an aspect, the present invention discloses a process of xylitol production wherein a thermo-tolerant and inhibitor tolerant *S. cerevisiae* DBT-IOC S24 (MTCC25086) natural strain has been induced to produce xylitol from xylose at defined process parameters using liquid extract of acid pretreated agricultural biomass, co-production of ethanol and xylitol from dilute acid pretreated lignocellulosic biomass as well as from xylose containing synthetic media in presence of glucose, lignocelluloses biomass derived xylitol inducer, maintaining aeration at 1VVM and pH at 5.0 in the medium.

BRIEF DESCRIPTION OF FIGURES

Other features, aspects, and advantages of the present invention will become better understood when the following detailed description is read with reference to the accompanying drawings in which like characters represent like parts throughout the drawings wherein.

DETAILED DESCRIPTION

Figure 1:
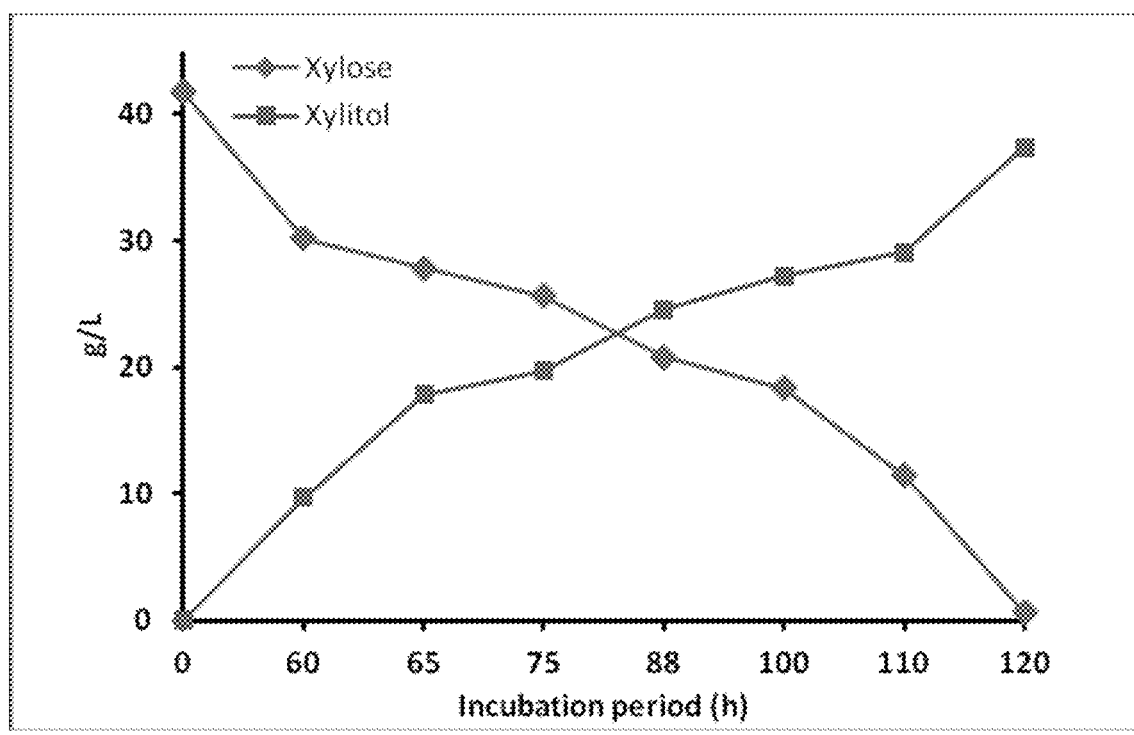
FIG. 1. Illustrates xylitol production by *S. cerevisiae* in pure xylose in synthetic medium.

For the purpose of promoting an understanding of the principles of the invention, reference will now be made to the embodiments illustrated in the figures and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates. Unless otherwise defined, all technical and scientific terms used herein have the same meaning as commonly understood by one of ordinary skilled in the art to which this invention belongs. The system, methods, and examples provided herein are illustrative only and not intended to be limiting.

The terminology and structure employed herein is for describing, teaching and illuminating some embodiments and their specific features, elements and does not limit, restrict or reduce the spirit and scope of the invention.

"Cellulase enzyme" used herein is a mixed form of enzyme which is mostly composed of exo-hydrolase, endo-hydrolase and beta-glucosidase. This enzyme was mostly produced from fungal sources. Cellulase breaks down the cellulose molecule into monosaccharide and shorter polysaccharides or oligosaccharides. In the present invention the cellulase enzyme is selected from commercially available cellulase enzyme which is suitable for the purposes.

LEPB (liquid extract pretreated biomass slurry) used herein as slurry containing liquid extract after dilute acid pre-treatment of lignocellulosic biomass. Liquid portion of slurry contains soluble sugar mainly xylose extracted from hemicellulose part of biomass. This liquid part of slurry also contains glucose and inhibitor (HMF, Furfural and other acids etc.).

Yeast is a single cell microorganism; prefer to grow on sugary surface and ferment sugars. Naturally yeast is mostly found on fruits and vegetables. It can grow at aerobic and partial anaerobic condition. *Saccharomyces cerevisiae* among the yeast group found most suitable for industrial application due to its unique characteristics.

In an aspect, the present invention provides a process of xylitol production from pure xylose, wherein said process comprises the steps of:
a) inoculating a natural thermo and inhibitor tolerant yeast strain (*Saccharomyces cerevisiae* DBT-IOC S24 (MTCC25086) in a synthetic medium containing 4% xylose, 1% glucose, 10 mM inducer, 0.2% of yeast extract and 0.1% peptone and incubating at a temperature of 37° C. and at 200 rpm;
b) adding 290-360 mg glucose and 8.0-12.0 mg inducer in every 15 min interval to one liter of fermented broth containing synthetic media as described above, after 6 h of fermentation;
c) maintaining aeration at 1VVM and pH at 5.0 in the medium;
d) obtaining xylitol yield of 99%;

In an embodiment, said natural thermo-tolerant and inhibitor tolerant yeast strain is *Saccharomyces cerevisiae* DBT-IOC S24 (MTCC25086).

In another embodiment, 300 mg glucose and 10 mg inducer (furfural/HMF) are added in every 15 min interval to one liter of fermented broth containing synthetic media as described above, after 6 h of fermentation, In yet another embodiment, said lignocelluloses biomass derived xylitol inducer is selected from furfural or HMF.

In one more embodiment, said synthetic fermentation medium comprises pure sugars, 0.2% of yeast extract, 0.1% peptone and furfural or HMF.

In an embodiment, said sugars comprise glucose and xylose in a combination ratio of 1:4.

In one embodiment, the present invention provides two step fermentation process for co-production of xylitol and ethanol, wherein the process comprises steps of:
diluting acid pretreated biomass using natural thermo and inhibitor tolerant yeast *S. cerevisiae* DBTIOC S24, strain;
adding cellulase enzyme 0.3 FPU/gTS (FPU per gram total solid) to 15% biomass solid loading at the initial stage of process to release glucose sugar during the process which facilitate xylose uptake by *Saccharomyces cerevisiae* DBT-IOC S24 and maintaining proper yeast cell growth;
obtaining xylitol conversion yield up to 99% of theoretical yield;
subjecting the remaining biomass for enzymatically hydrolysis by adding cellulase at 2.0 FPU/gTS at 50° C.; followed by fermentation for ethanol production by inoculating yeast *S. cerevisiae* DBTIOC S24;
obtaining 21 g/L ethanol concentration at 37° C. by *Saccharomyces cerevisiae* DBT-IOC S24 (MTCC25086), after final fermentation.

In a second aspect, the present invention provides a process of xylitol production from acid pretreated biomass wherein said process comprises steps of:
a) inoculating natural thermo-tolerant and inhibitor tolerant yeast strain (*Saccharomyces cerevisiae* DBT-IOC S24 (MTCC25086)) at concentration of 2 g/L cell to dilute acid pretreated biomass (15% gTS);
b) adding at the initial stage of fermentation 0.3 FPU/gTS cellulase enzyme to the fermentation process to release glucose sugar during the process which facilitate xylose uptake and maintained proper yeast cell growth;
c) maintaining aeration to 1VVM and pH at 5.0 during fermentation process;
d) subjecting the biomass after xylitol production biomass to enzymatic hydrolysis using 2.0 FPU/gTS (cumulative enzyme dose in the process 2.3 FPU/gTS) at 50° C.

Having described the basic aspects of the present invention, the following non-limiting examples illustrate specific embodiment thereof.

Example-1

*S. cerevisiae* DBT-IOC S24 is inoculated to a synthetic medium containing pure sugars [glucose (1%) and xylose (4%) in a combination 1:4 ratio], yeast extract (0.2%), peptone (0.1%) along with inducers (HMF or/and furfural) at 10 mM concentration. The yeast was inoculated to the fermentation medium at 2 g/L cell concentration and incubated at 37° C. and 200 rpm. After 6 h of fermentation, 290-360 mg glucose and 8.0-12.0 mg inducer (furfural/HMF) are added in every 15 min interval to one liter of fermented broth containing synthetic media as described above. Aeration and pH of the culture medium maintained to 1VVM and 5.0, respectively throughout the fermentation. Every 24 h interval the samples are estimated through HPLC for detection of xylitol (FIG. 1).

Example-2

Figure 2:
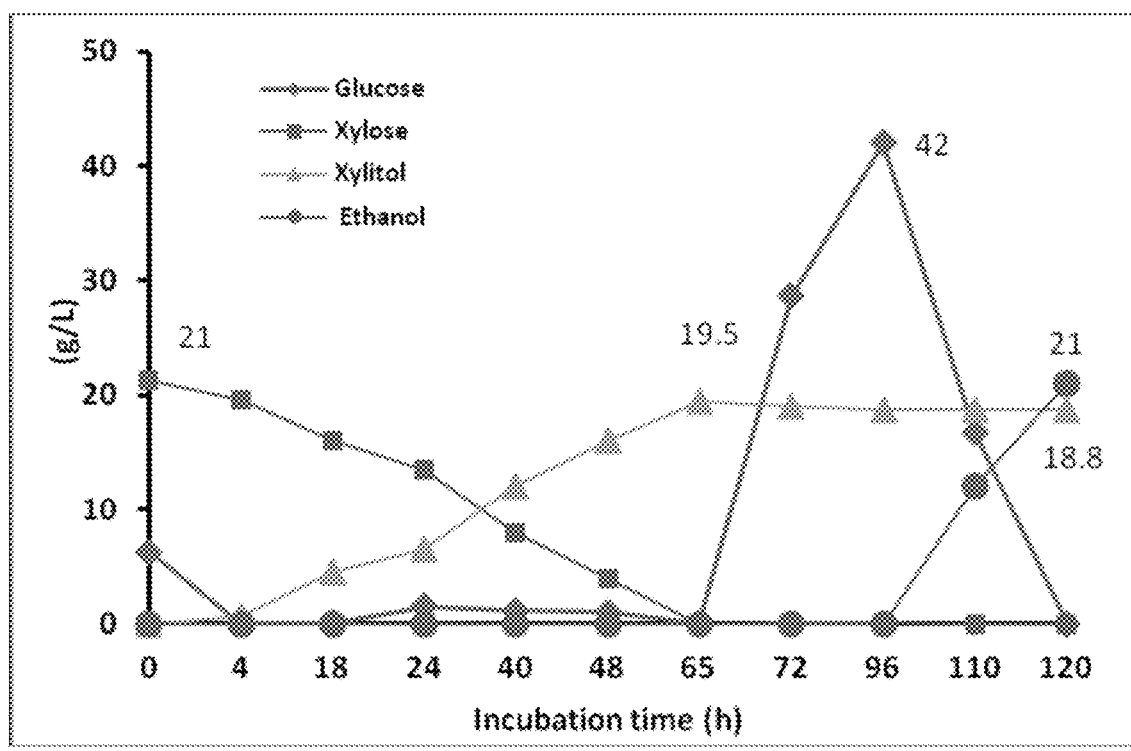
FIG. 2 Illustrates co-production of xylitol and ethanol production by *S. cerevisiae* in two step fermentation process operated with acid pretreated lignocellulosic biomass.
Figure 3:
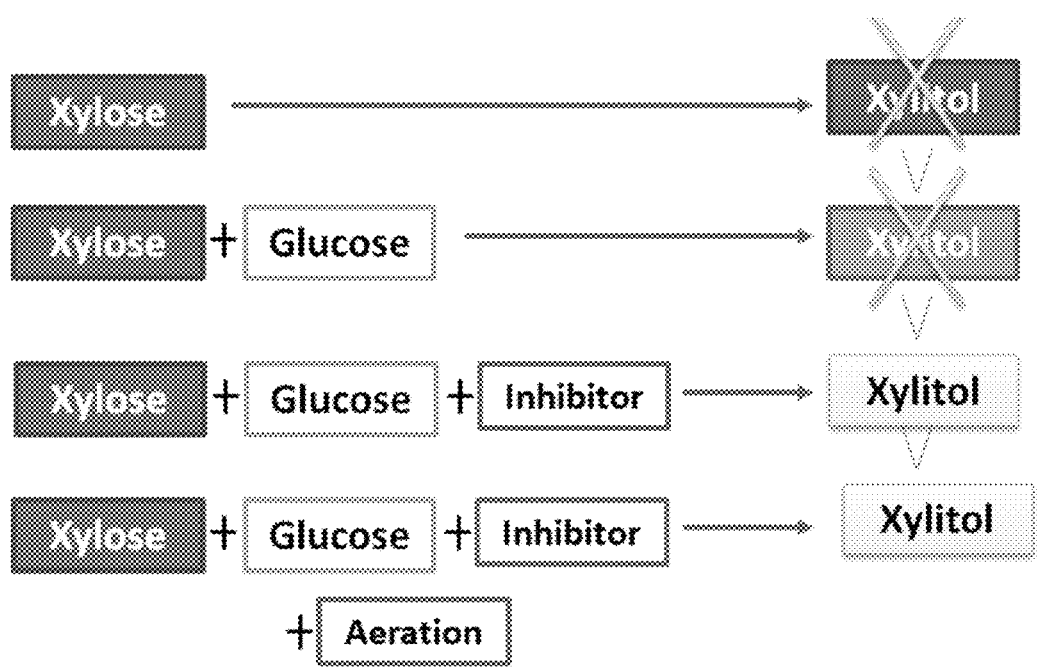
FIG. 3 Illustrates systematic presentation for xylitol production by *S. cerevisiae* from xylose in synthetic medium.

Xylitol production was observed in acid pretreated biomass by inoculating natural *S. cerevisiae*, to the non-detoxified biomass, at 37° C. for 50 to 65 h. At the initial stage of fermentation, 0.3 FPU/gTS cellulase enzyme added to the fermentation process to release sugar during the process which facilitate xylose uptake and maintained proper yeast cell growth. Similar xylitol conversion yield (99% of theoretical yield) is also observed in this fermentation process compared to pure xylose fermentation in synthetic medium. After the xylitol production biomass may subject to enzymatic hydrolysis by using 2.0 FPU/gTS (cumulative enzyme dose in this process 2.3 FPU/gTS) at 50° C. and followed by fermentation for ethanol (21 g/L) production at 37° C. by the same yeast strain. In this experiment there is no external addition of inducers (HMF or/and furfural) to the process because the inducers are preexisting in the pretreated biomass and the existing concentration was sufficient enough for the xylitol induction by S. cerevisiae DBT-IOC S24. (FIG. 2).

The present invention reports xylitol conversion yield almost close to theoretical yield for xylitol with titer of 37 g/l. Overall xylitol production is 99% comparing to initial xylose concentration of maximum theoretical yield 0.91 g/g of xylitol production from xylose under aerobic condition (Barbosa et al., 1988) in the fermentation broth.

Comparative analysis has been provided in the below given tables, showing that the process of the present invention is efficient in terms of yield of xylitol alone, combined production of xylitol and ethanol compared to other processes known in the art.

TABLE 1

Co-production of xylitol and ethanol by different yeast strains

| Organism | Xylitol production (g/g) | Ethanol production (g/g) | References |
|---|---|---|---|
| Candida tropicalis | 0.39 | 0.48 | Hickert et al. (2013) |
| Saccharomyces cerevisiae | 0.57 | 0.33 | Cortivo et al. (2018) |
| Kluyveromyces marxianus | 0.315 | 0.44 | Dasgupta et al. (2017) |
| Co-culture of S. cerevisiae and Candida tropicalis | 0.55 | 0.44 | Zahed et al., (2016) |
| Candida tropicalis | 0.50 | 0.74 | Swain and Krishnan (2015) |
| Saccharomyces cerevisiae (wild strain) | 0.89 | 100% ethanol conversion of glucose produced during hydrolysis | Present invention |

TABLE 2

Xylose to xylitol production by different yeast strains:

| Name of microorganism | Genetically modification/ or not | Xylitol production g/g | Actual Yield compared to theoretical yield | Reference |
|---|---|---|---|---|
| Candida sp. | Natural strain | 0.8 g/g | 87% | US8921082B2 |
| Candida tropicalis (NRRL 12968) | Natural strain | 0.7 g/g | 76% | US20150218598A1 |
| Debaryomyces hansenii | Natural stain | 0.81 g/g | 87% | Converti and Dominguez, 2001 |
| Debaryomyces hansenii UFV-170 | Natural stain | 0.74-0.77 g/g | 80.7-84% | Sampaio et al., 2006 |
| Candida guillermondii | Natural stain | 0.63 g/g | 69% | Meyrial et al., 1991 |
| Saccharomyces cerevisiae | Genetically modified | — | 95% | Hallborn et l., 1991 |
| Saccharomyces cerevisiae | Natural strain | 0.89 g/g | 98% | Present Invention. |

REFERENCES OF TABLE

1. Hickert, Souza-Cruz, P. B., Rosa, C. A., Ayub, M. A. Z., 2013. Simultaneous saccharification and co-fermentation of un-detoxified rice hull hydrolysate by Saccharomyces cerevisiae ICV D254 and Spathaspora arborariae NRRL Y-48658 for the production of ethanol and xylitol. Bioresour. Technol. 43, 112-116.
2. Cortivo, Paulo Roberto Dall, Hickert, L. R., Hector, R., Ayub, M. A. Z., 2018. Fermentation of oat and soybean hull hydrolysates into ethanol and xylitol by recombinant industrial strains of Saccharomyces cerevisiae under diverse oxygen environments. Ind. Crops Prod. 113, 10-18.
3. Dasgupta D., Ghosh D., Bandhu S., Adhikari D. K. (2017) Lignocellulosic sugar management for xylitol and ethanol fermentation with multiple cell recycling by Kluyveromyces marxianus IIPE453. Microbiological Research, 200, 64-72.
4. Zahed, O., Jouzani, G. S., Abbasalizadeh, S. et al. (2016). Continuous co-production of ethanol and xylitol from rice straw hydrolysate in a membrane bioreactor. Folia Microbiol 61, 179-189.
5. Swain M. R., Krishnan C. (2015) Improved conversion of rice straw to ethanol and xylitol by combination of moderate temperature ammonia pretreatment and sequential fermentation using Candida tropicalis. Industrial Crops and Products 77, 1039-1046.
6. U.S. Pat. No. 9,228,178B2: Engineering of xylose reductase and overexpression of xylitol dehydrogenase and xylulokinase improves xylose alcoholic fermentation in the thermotolerant yeast Hansenula polymorpha.
7. US20070141690A1: Mutant Saccharomyces cerevisiae strain utilizing xylose for ethanol production.
8. Converti A., Dominguez J. M. Influence of temperature and pH on xylitol production from xylose by Debaryomyces hansenii. 2001, 75, 39-45.
9. Sampaio F. C., Moraes, C. A., De Faveri D., Perego P., Converti A., Passos F. M. L. Influence of temperature and pH on xylitol production from xylose by Debaryomyces hansenii UFV-170. Process Biochemistry, 2006, 41, (3)675-681.
10. Converti A., Dominguez J. M. Influence of temperature and pH on xylitol production from xylose by Debaryomyces hansenii. 2001, 75, 39-45.

11. Hallborn J., Walfridsson M., Airaksinen U., Ojamo H., Hägerdal B. H., Penttilä M. Keränen S. Xylitol Production by Recombinant *Saccharomyces Cerevisiae.Bio/Technology* 1991, 9, 090-1095.
12. Lee W. J., Ryu Y. W., Seo J. H. Characterization of two-substrate fermentation processes for xylitol production using recombinant *Saccharomyces cerevisiae* containing xylose reductase gene. Process Biochemistry.2000, 35, 10, 1199-1203.
13. Meyrial, V., Delgenes, J. P., Moletta, R. et al. Xylitol production from D-xylose by *Candida guillermondii*: Fermentation behaviour. *Biotechnol Lett* 0.1991, 13, 281-286.

It will thus be seen that the objects set forth above, among those made apparent from the preceding description, are efficiently attained, and since certain changes may be made in the constructions set forth without departing from the spirit and scope of the invention, it is intended that all matter contained in the above description shall be interpreted as illustrative and not in a limiting sense. The invention has been described with reference to preferred and alternate embodiments. Modifications and alterations will become apparent to those skilled in the art upon reading and understanding the detailed discussion of the invention provided herein. This invention is intended to include all such modifications and alterations in so far as they come within the scope of the present invention. These and other modifications of the preferred embodiments as well as other embodiments of the invention will be obvious from the disclosure herein, whereby the foregoing descriptive matter is to be interpreted merely as illustrative of the invention and not as a limitation.

Finally, to the extent necessary to understand or complete the disclosure of the present invention, all publications, patents, and patent applications mentioned herein are expressly incorporated by reference therein to the same extent as though each were individually so incorporated.

What is claimed is:

1. A process of xylitol production from pure xylose, wherein said process comprises the steps of:
   a) inoculating a natural thermo- and inhibitor tolerant yeast strain having concentration of 10 mM inducer in a synthetic fermentation medium containing 4% xylose, 1% glucose, 0.2% of yeast extract and 0.1% peptone and incubating at a temperature of 37° C. and at 200 rpm;
   b) adding 290-360 mg glucose and 8.0-12.0 mg inducer in every 15 min interval to one liter of fermented broth containing synthetic media as described above, after 6 h of fermentation;
   c) maintaining aeration at 1VVM and pH at 5.0 in the medium; and
   d) obtaining xylitol yield of 99%.

2. The process as claimed in claim 1, wherein said natural thermo and inhibitor tolerant yeast strain is *Saccharomyces cerevisiae* DBT-IOC S24 (MTCC25086).

3. The process as claimed in claim 1, wherein 300 mg glucose and 10 mg inducer are added in every 15 min interval to one liter of fermented broth containing synthetic media, after 6 h of fermentation.

4. The process as claimed in claim 1, wherein said lignocelluloses biomass derived xylitol inducer is selected from furfural or HMF.

5. The process as claimed in claim 1, wherein said sugars comprises glucose and xylose in a combination ratio of 1:4.

6. The process as claimed in claim 1, wherein the fermentation is carried out for 120-140 h at 37° C. for obtaining xylitol with a yield of 0.89 g/g.

7. A process of xylitol production from liquid extract from dilute acid pretreated biomass (LEPB), wherein said process comprises steps of:
   a) inoculating a natural thermo and inhibitor tolerant yeast strain (*Saccharomyces cerevisiae* DBT-IOC S24 (MTCC25086)) at concentration of 2 g/L cell to liquid extract from dilute acid pretreated biomass containing 4% xylose, 1% glucose, major inducers selected from furfural or HMF;
   b) maintaining aeration to 1VVM and pH at 5.0 during fermentation process;
   c) Obtaining xylitol yield of 99%.

8. The process as claimed in claim 7, wherein the fermentation is carried out for 120-140 h at 37° C. for obtaining xylitol with a yield of 0.89 g/g.

9. The process as claimed in claim 7, wherein said liquid extract from dilute acid pretreated biomass (LEPB) contains 4% xylose, 1% glucose, major inducers selected from furfural or HMF.

10. The process as claimed in claim 9, wherein concentration of inducers ranges between 0.5 to 1.2 g/L depending on severity of pre-treated biomass.

11. A two-step fermentation process for co-production of xylitol and ethanol from acid pretreated biomass, wherein the process comprises steps of:
   diluting acid pretreated biomass using natural thermo and inhibitor tolerant yeast *Saccharomyces cerevisiae* DBT-IOC S24 (MTCC25086), strain;
   adding cellulase enzyme 0.3 FPU/TS to 15% biomass solid loading at the initial stage of process to release glucose sugar during the process which facilitate xylose uptake by *Saccharomyces cerevisiae* DBT-IOC S24 (MTCC25086) and maintaining proper yeast cell growth;
   obtaining xylitol conversion yield up to 99% of theoretical yield;
   subjecting the remaining biomass for enzymatically hydrolysis by adding cellulase at 2.0 FPU/gTS at 50° C. for 31 h; followed by fermentation for ethanol production by inoculating yeast *Saccharomyces cerevisiae* DBT-IOC S24 (MTCC25086) from glucose sugar;
   obtaining 21 g/L ethanol concentration at 37° C. by *Saccharomyces cerevisiae* DBT-IOC S24 (MTCC25086), after final fermentation.

\* \* \* \* \*